United States Patent [19]

Azuma et al.

[11] 4,243,663
[45] Jan. 6, 1981

[54] GLYCOLIPID COMPOSITIONS FOR TRANSPLANTED TUMOR IMMUNOTHERAPY

[76] Inventors: Ichiro Azuma, 1-2, Aoyamadai, Suita-shi; Yuichi Yamamura, 1-9-22, Nikawa-takadai, Takarazuka-shi, both of Japan

[21] Appl. No.: 931,050

[22] Filed: Aug. 4, 1978

Related U.S. Application Data

[63] Continuation-in-part of Ser. No. 809,884, Jun. 24, 1977, abandoned.

[30] Foreign Application Priority Data

Jun. 25, 1976 [JP]  Japan ................................ 51-75866
Aug. 9, 1977 [JP]  Japan ................................ 52-95404

[51] Int. Cl.³ .................... C07H 13/02; A61K 31/71; A61K 31/72
[52] U.S. Cl. ........................... 424/181; 424/92; 424/180; 536/116; 536/119
[58] Field of Search ............ 424/92, 180, 181; 536/119

[56] References Cited

U.S. PATENT DOCUMENTS

| | | | |
|---|---|---|---|
| 3,597,417 | 8/1971 | Myhre | 536/119 |
| 3,631,025 | 12/1971 | Martin | 536/119 |
| 3,634,397 | 1/1972 | Thompson et al. | 536/119 |
| 3,839,555 | 10/1974 | Billiau et al. | 424/92 |

*Primary Examiner*—Johnnie R. Brown
*Attorney, Agent, or Firm*—Wolder, Gross & Yavner

[57] ABSTRACT

A composition which is capable of specifically inducing an immunity when administered into the body of a host in association with a tumor antigen, or which is capable of non-specifically enhancing an immunizing function when administered into the body of a tumor-carrying host, comprising a glycolipid as active ingredient in association with a pharmaceutically acceptable carrier, wherein the saccharide moiety of the glycolipid is selected from the group consisting of fructose, glucose and sucrose.

11 Claims, No Drawings

GLYCOLIPID COMPOSITIONS FOR TRANSPLANTED TUMOR IMMUNOTHERAPY

RELATED APPLICATIONS

This application is a continuation-in-part of U.S. Ser. No. 809,884, filed June 24, 1977, now abandoned, for the present inventors.

SUMMARY OF THE INVENTION

The present invention relates to agent for the immunotherapy against tumors of animal subject, said agent containing a glycolipid as active ingredient. It has been known in the art that certain glycolipids are active upon inhibiting the growth of tumor cells of animals. For example, it has been known that a fatty acid ester of trehalose produced by a bacterium belonging to the genus Mycobacterium and designated as "cord factor" exhibits adjuvant activity and also inhibits, as itself, the growth of certain tumor cells [Science, 174, 1240–1242 (1971); Int. J. Cancer, 16, 442–447(1975); and Cancer Immunol. Immunother., 1, 227–232 (1976)]. However, this cord factor has practically never been used as adjuvant or other medicament because of its excessively high toxicity.

The term "adjuvant" as used in the specification denotes a substance which is capable of specifically inducing an immunity when administered into the body of a host in association with a tumor antigen, or which is capable of non-specifically enhancing an immunizing function when administered into the body of a tumor-carrying host.

The present invention is directed to provide a composition having adjuvant activity (as hereinbefore defined). The present invention provides a composition having adjuvant activity, comprising a glycolipid as active ingredient in association with a pharmaceutically acceptable carrier, the saccharide moiety of said glycolipid being selected from the group consisting of fructose, sucrose and glucose.

The invention will be more fully understood by the following description.

The fructolipid, sucrolipid and glucolipid viz. fatty acid esters of fructose, sucrose and glucose which may be used for the purpose of the present invention are exemplified by the following formulae:

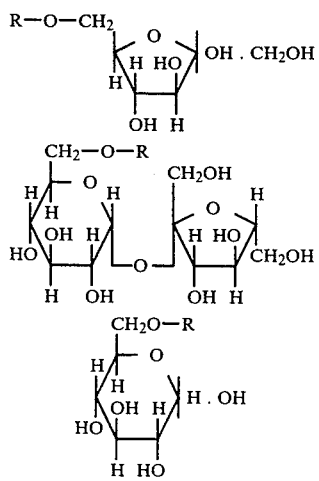

wherein R is a residual group of an acid selected from mycolic acid, nocardomycolic acid and corynomycolic acid.

The basic structure of these fatty acids may be represented by the following formula:

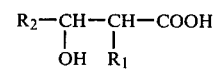

wherein $R_1$ and $R_2$ are alkyl groups.

With respect to the numbers of carbon atoms, these acids may be classified as follows.

| Acid | $R_1$ | $R_2$ |
|---|---|---|
| Mycolic acid | various alkyl groups of $C_{20-24}$, mainly $C_{22}$ | various alkyl groups of 2–8 types ($C_{41-67}$) |
| Nocardomycolic acid | various alkyl groups of $C_{10-18}$, mainly $C_{12-14}$ | various alkyl groups of 2–8 types ($C_{21-41}$) |
| Corynomycolic acid | various alkyl groups of $C_{10-18}$, mainly $C_{12-14}$ | various alkyl groups of 2–8 types ($C_{11-23}$) |

The main peaks of carbon atoms of $R_1$ and $R_2$ of glycolipids originated from certain microorganisms are exemplified as follows.

| Acid | $R_1$ | $R_2$ | Origin |
|---|---|---|---|
| Mycolic acid | 20 & 22 | 57,59,61 & 63 | Mycobacterium avium |
| | 20 & 22 | 55,57,59, & 61 | M. paraffinicum |
| Nocardomycolic acid | 12 & 14 | 35,37, & 39 | Nocardia rubra |
| | 12 & 14 | 33,35 & 37 | N. paraffinica |
| Corynomycolic acid | 12 | 17.19 & 21 | Corynebacterium hydrocarboclastus |
| | 12 & 14 | 19,21 & 23 | Arthrobacter paraffineus |

The production and recovery of these glycolipids are known per se. For example, they may be carried out according to the methods described as follows, in Japanese Patent Publication No. 7349/72 and Japanese patent application laid open to public inspection as No. 48186/75 (corresponding to U.S. Pat. Nos. 3,637,461 and 3,909,356, respectively).

A microorganism which belongs to the genus Arthrobacter, Corynebacterium, Nocardia or Mycobacterium and which is capable of producing the glycolipid by metabolizing a corresponding saccharine material as main carbon source, is cultured in a medium containing the corresponding saccharine material as the main carbon source under aerobic conditions to accumulate the glycolipid in the medium or microbial bodies, from which the glycolipid is recovered.

Certain microorganisms which are preferred are exemplified as follows.

| | |
|---|---|
| Arthrobacter paraffineus | ATCC 15591 |
| Arthrobacter hydrocarboglutamicus | ATCC 15583 |
| Arthrobacter roseoparaffineus | ATCC 15584 |
| Arthrobacter simplex | ATCC 15799 |
| Corynebacterium hydrocarboclastus | ATCC 15592 |
| Corynebacterium hydrocarboclastus | ATCC 21628 |
| Corynebacterium pseudodiphtheriticum | ATCC 10701 |
| Nocardia paraffinica | ATCC 21198 |
| Nocardia globerula | ATCC 13130 |
| Nocardia rubra | IFM 18; NRRL 11094 |
| Mycobacterium rubrum | ATCC 14346 |
| Mycobacterium paraffinicum | ATCC 12670 |

| | |
|---|---|
| *Mycobacterium smegmatis* | ATCC 21293 |
| *Mycobacterium smegmatis* | ATCC 12297 |
| *Mycobacterium avium* | IFO 3153; NRRL B-11095 |

The above microorganisms having ATCC number are on deposit with the American Type Culture Collection, 12301 Parklawn Dr., Rockville, Md. 20852 U.S.A. and are freely available therefrom.

The culturing method for these microorganims is known per se. For example, a large amount of glycolipid is obtained when the fermentation is effected at 25-40° C. and at a pH of 4-9 (preferably 6-8) for 1-7 days. The recovering method is also known per se. In this manner, the glycolipids represented by the formulae [I], [II] and [III] wherein $R_1$ and $R_2$ are as hereinbefore defined may be produced.

For example, when *Arthrobacter paraffineus* (ATCC 15591) is cultured by using sucrose as main carbon source, it is possible to obtain sucrolipid represented by the following formulae [IV] and [V]:

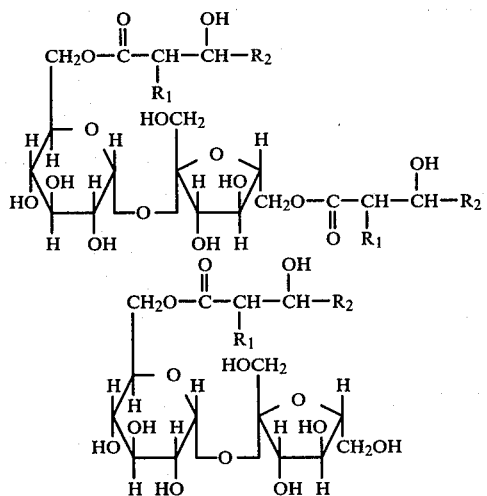

wherein $R_1$ is a $C_{10}$ to $C_{18}$ alkyl group and $R_2$ is a $C_{11}$ to $C_{23}$ alkyl group.

When fructose is used as main carbon source for culturing the same microorganism, it is possible to obtain fructolipids represented by the following formulae [VI] and [VII]:

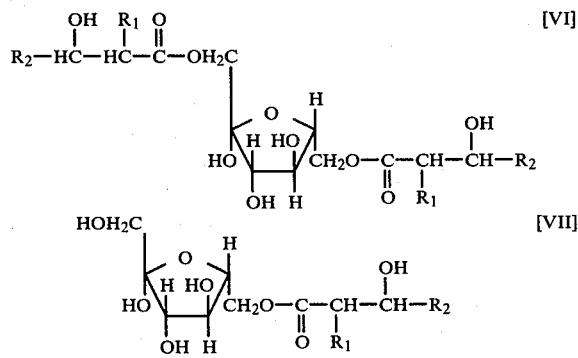

wherein $R_1$ is a $C_{10}$ to $C_{18}$ alkyl group and $R_2$ is a $C_{11}$ to $C_{23}$ alkyl group.

When *Corynebacterium hydrocarboclastus* (ATCC 21628) is cultured, it is possible to obtain the glycolipids of the formulae [IV] and [V] as hereinbefore defined by using sucrose as main carbon source, and the glycolipids of the formulae [VI] and [VII] as hereinbefore defined by using fructose as main carbon source, respectively.

Any of a variety of conventional pharmaceutically acceptable carriers such as plant or mineral oils, surfactants, physiological salt solutions and the like may be used.

Examples of suitable carriers include a mineral oil such as Drakeol 6VR (commercial product of Pennsylvania Refining Co., U.S.A.); a plant oil such as olive oil and peanut oil; physiological solution of sodium chloride; a surfactant such as Tween 80 (commercial product of Atlas Chemical Industries, Inc., U.S.A.); Freund's incomplete adjuvant (an emulsion of water-in-oil) and the like. These carriers may be used in conventional manner to prepare the composition of the present invention.

The present composition comprises the glycolipid of the invention at a concentration of from 10 γ to 10 mg per ml, preferably from 100 γ to 2 mg per ml. It may be administered sub- or intracutaneously, intramuscularly, intraveneously, intraperitioneally or intrapleurally. If desired, it is also possible to administer the composition topically into the tumor in the body of the patient. The amount of the glycolipid to be administered is from 10 γ to 10 mg (usually from 100 γ to 300 γ) in one week, based upon an average mammal weighing approximately 60 kg, although the entire dosage and the interval may be dependent upon the response of the patient.

The composition of the present invention may be used solely. It is also possible to use it in association with suitable tumor cells which may, if desired, be inactivated previously by, for example, treating with radioactive rays, anticancer agents (such as mitomycin) and the like. In this case, the amount of the tumor cells is usually from $10^5$ to $10^8$ cells (based upon average mammal weighing approximately 60 kg).

It is also possible to use the agent of the present invention in association with a tumor antigen which is preferably obtainable from the cell wall of a microorganism of the species *Propionibacterium acnes, Nocardia rubra* and/or BCG.

The pharmaceutical composition of the invention is conveniently in a form suitable for administration. Thus the pharmaceutical carrier or excipient is preferably sterile. The composition is advantageously contained in ampoules or vials, each ampoule or vial preferably containing from 2 γ to 50 mg, for example, from 2 γ to 10 mg, especially from 4 to 300 γ of the said glycolipid. The ampoule or vial preferably contains approximately the same amount of tumor antigen as glycolipid.

The pharmaceutical composition may, for example, be in dosage unit form (as hereinafter defined) e.g. in the form of tablets, pills or capsules. Each dosage unit form preferably contains from 2 γ to 50 mg, for example, from 2 γ to 10 mg, especially from 4 to 300 γ of the said glycolipid.

The term "dosage unit" as hereinbefore defined means a pharmaceutical composition of the present invention in a form adapted to provide a single or unitary dosage of the said active ingredient. Thus, for example, pills and capsules may be in a form adapted to provide a single or unitary dose of the said active ingredient and thus such tablets, pills, capsules and ampoules may be considered to be in dosage unit form. Each dosage unit preferably contains approximately the same amount of tumor antigen as glycolipid.

Where the composition in the form of drops, syrups, emulsions or spray compositions, such compositions preferably contain from 10 γ to 10 mg/ml, especially from 100 γ to 2 mg/ml of the said glycolipid. Such compositions preferably contain approximately the same amount of tumor antigen as the glycolipid.

The composition according to the present invention is active upon enhancing the immunity effected by protein antigen such as for example α-amylase, egg white albumin, phytohemmaglutinin and the like, as well as upon the immunity of various tumor antigen, with low toxicity. Also, the composition may be useful for immunotherapy against tumors such as leukemia, sarcoma, melanoma and the like in animal subject.

The activity of the adjuvant composition according to the present invention was determined by using guinea pigs and mice as test animals. The results are shown in the following examples, in which the activity is in general indicated by the enhancing activity upon the delayed-type hypersensitive reaction or upon the formation of the body liquid-type antibody. The effects are apparent from the following examples, in which the glycolipids used had an $LD_{50}$ of more than 250 mg/kg and were prepared in conventional manner as described in U.S. Pat. Nos. 3,637,641 and 3,909,356, which are incorporated by reference.

For comparative purpose, a trehalolipid (cord factor) was prepared by using a strain of *Mycobacterium tuberculosis* Aoyama B in a conventional manner as is described in Journal of The National Cancer Institute, 52, 95-101 (1974). This trehalolipid had an $LD_{50}$ of 1.5 mg/kg. The glycolipids used in the examples were prepared in a similar manner to that described in Japanese patent application No. 7349/72 and Japanese patent application laid open to public inspection as No. 48186/75.

Preparation of Glycolipids

*Arthrobacter paraffineus* (ATCC 15591) was cultured with shaking in a medium containing sucrose (3 g/dl), meat extract (1.0 g/dl), peptone (1.0 g/dl) and sodium chloride (0.3 g/dl) and having a pH of 7.2 before sterilization at a temperature of 30° C. for 24 hours, and was then inoculated into another medium (3.0 liter) put in a 5 liter jar fermentor at a ratio of 10% by volume. This medium had the following composition:
$NaHPO_4.12H_2O$ (0.2 g/dl), $MgSO_4.7H_2O$ (0.1 g/dl), $FeSO_4.7H_2O$ (0.05 g/dl), $ZnSO_4.7H_2O$ (0.0001 g/dl), corn steep liquor (0.3 g/dl), $KH_2PO_4$ (0.2 g/dl), $(NH_4)_2SO_4$ (0.5 g/dl), $MnSO_4.4H_2O$ (0.002 g/dl), $CaCl_2.2H_2O$ (one mg/l) and sucrose (10 g/dl).

The fermentation was effected at 30° C. for 45 hours with shaking (600 r.p.m.) and aeration of sterilized air (one liter/liter/minute). The pH of the medium was automatically adjusted to 6.8-7.2 with ammonia. After completion of the fermentation, the cultured liquor (2.8 liter) was centrifuged to give microbial bodies (250 g by wet weight) which were extracted with a mixture of chloroform and methanol (1:1) 3 times. The extracted solution (3 liter) was then concentrated by flash evaporation and the residue was extracted with chloroform (100 ml). The solvent was evaporated off and the residue was dissolved in n-hexane (21 ml). By centrifuging of the solvent, there was obtained an n-hexane solution (20 ml) containing a mixture of each two types of sucrose esters and of phospholipids. The solution was transferred to a column (inner diameter 4 cm; height 20 cm) packed with silica gel (commercially available from Mallinkrodt Chemical Works, U.S.A.). Chloroform (1200 ml) was passed through the column to elute pigments and liberated fatty acids, and a mixture of chloroform (99-93) and methanol (1-7) (1500 ml) was passed through the column to elute fractions (each 50 ml). Fraction Nos. 15-27 were collected and combined, from which the solvent was removed. The residue was dissolved in warm acetone (15 ml) and allowed to stand while cooling with ice to give precipitates which were then washed with cold acetone (20 ml). After drying there were obtained white powders (1.1 g) which represented sucrolipids (corynomycolic acid) used in the following examples, viz, the sucrolipids of the formula [II] as hereinbefore defined, in which R was a residue of corynomycolic acid, in which $R_1$ was various alkyl groups having carbon atoms of 10-18 (main peaks at 12 and 14) and $R_2$ was various alkyl groups having carbon atoms of 11-23 (main peak at 23).

Glucolipids (mycolic acid) used in the examples may be produced in a similar manner to that described above with the exception that glucose is used instead of sucrose and that *Mycobacterium avium* (IFO 3153; NRRL B-11095) is used instead of *Arthrobacter paraffineus* (ATCC 15591). The thus-produced glucolipids correspond to the glucolipids of the formula [III] as hereinbefore defined, in which R is a residue of mycolic acid, in which $R_1$ is various alkyl groups having carbon atoms of 20-24 (main peak at 22) and $R_2$ is various alkyl groups having carbon atoms of 41-67 (main peaks at 57, 59, 61 and 63).

Fructolipids (mycolic acid) used in the examples may be produced in a similar manner to that described in the above-mentioned reference with the exception that *Mycobacterium avium* (IFO 3153; NRRL B-11095) is cultured instead of *Arthrobacter paraffineus* (ATCC 15591) and that fructose is used instead of sucrose. The thus-obtained fructolipids correspond to the fructolipids of the formula [I] as hereinbefore defined, in which R is a residue of mycolic acid, in which $R_1$ is various alkyl groups having carbon atoms of 20-24 (main peaks at 20 and 22) and $R_2$ is various alkyl groups having carbon atoms of 41-67 (main peaks at 61 and 63).

Fructolipids (corynomycolic acid) used in the examples may be produced in a similar manner to that described in the above-mentioned reference with the exception that fructose is used instead of sucrose. The thus-produced fructolipids correspond to the fructolipids of the formula [I] as hereinbefore defined, in which R is a residue of corynomycolic acid, in which $R_1$ is various alkyl groups having carbon atoms of 10-18 (main peaks at 12 and 14) and $R_2$ is various alkyl groups having carbon atoms of 11-23 (main peaks at 19.21 and 23).

A similar treatment to that described above was repeated to produce the fructolipids of the formula [I] as hereinbefore defined, in which R was a residue of nocardomycolic acid, with the exception that *Nocardia rubra* (NRRL 11094) was used instead of *Arthrobacter paraffineus* (ATCC 15591).

A similar treatment to that described above was repeated to produce the sucrolipids of the formula [II] as hereinbefore defined, in which R was a residue of corynomycolic acid, with the exception that *Corynebacterium hydrocarboclastus* (ATCC 21628) was used instead of *Arthrobacter paraffineus* (ATCC 15591).

EXAMPLE 1

Enhancing activity upon the delayed-type hypersensitive reaction (skin reaction test)

Glycolipids shown in Table 1 were used as test samples.

TABLE 1

|  | Guinea pig | Skin reaction test (mm/mm) after 4 hours | after 48 hours |
|---|---|---|---|
| Trehalolipid** | 1 | 16 × 16 | 17 × 14 |
| (mycolic acid)* | 2 | 15 × 15 | 16 × 14 |
|  | 3 | 17 × 17 | 15 × 12 |
|  | 4 | 15 × 15 | 14 × 10 |
| Sucrolipid | 1 | 22 × 22 | 20 × 16 |
| (corynomycolic | 2 | 20 × 20 | 19 × 18 |
| acid)* | 3 | 18 × 18 | 15 × 11 |
|  | 4 | 17 × 17 | 13 × 13 |
| Glucolipid | 1 | 20 × 20 | 20 × 14 |
| (mycolic acid)* | 2 | 20 × 20 | 19 × 14 |
|  | 3 | 18 × 18 | 15 × 15 |
|  | 4 | 16 × 16 | 14 × 13 |
| Fructolipid | 1 | 18 × 18 | 20 × 20 |
| (mycolic acid)* | 2 | 16 × 16 | 19 × 18 |
|  | 3 | 14 × 14 | 19 × 17 |
|  | 4 | 14 × 14 | 16 × 13 |
| Fructolipid | 1 | 16 × 16 | 16 × 14 |
| (corynomycolic | 2 | 15 × 15 | 14 × 12 |
| acid)* | 3 | 15 × 15 | 13 × 10 |
|  | 4 | 15 × 15 | 10 × 8 |
| No additive | 1 | 20 × 20 | 4 × 4 |
| (control) | 2 | 18 × 18 | 7 × 7 |
|  | 3 | 18 × 18 | 0 × 0 |

**Reference adjuvant
*Fatty acid moiety

A mixture of a glycolipid (300 μg) and a bacterial α-amylase (300 μg; prepared from *Bacillus subtilis* which was available commercially from Seikagaku Kogyo K.K., Tokyo) was homogenized after addition of a smallest possible amount of Drakeol 6VR (a mineral oil available commercially from Pennsylvania Refining Co., U.S.A.). After this, a physiological solution of sodium chloride containing Tween 80 (a surfactant available from Atlas Chemical Industries Inc., U.S.A., a commercial product) was added to the mixture in an amount that gave a final concentration of 0.2% and was further homogenized to give an oil-in-water type mixture.

Some groups of guinea pigs, each consisting of 4 guinea pigs (weight 250-300 g), were used as test animals, each of which was immunized by intramuscular injection of the oil-in-water type mixture (0.2 ml in total) in four footpads.

After 4 weeks, a physiological solution of sodium chloride (0.1 ml) containing the said α-amylase (100 μg) was intradermally administered to each of the test animals at its back to investigate the skin reaction. The results are shown in Table 1 wherein the skin reaction is evaluated by the sizes of the erythemata after 4 hours and the induration after 48 hours from the injection of the skin antigen to be determined.

A known trehalolipid and the antigen without addition of the glycolipid were used for reference and control purposes respectively. In Table 1 and the following tables, the fatty acid in each of the glycolipid is indicated in the parenthesis.

EXAMPLE 2

Glycolipids shown in Table 2 were used in the test which was carried out in a similar manner to that described in a report by Okada et al [J. Biochem., 54, 477-483 (1963)].

A smallest possible amount of Drakeol 6VR was added to a mixture of a glycolipid (300 μg) and a bacterial α-amylase prepared from *Bacillus subtilis* (300 μg). The mixture was homogenized and was added with a physiological solution of sodium chloride which contained Tween 80 in such an amount that gave a final concentration of 0.2%. The mixture was further homogenized to give an oil-in-water type mixture.

Some groups of guinea pigs, each consisting of 4 guinea pigs (weight 200-300 g), were used as test animals, each of which was immunized by intramuscular injection of the oil-in-water type mixture (0.2 ml in total) into four footpads. A blood sample (25 μl) was collected and centrifuged to give a serum sample (13 μl) which was then diluted [×20, ×100 and ×1,000] with physiological solution of sodium chloride. The diluted serum was mixed with the bacterial α-amylase (0.6 μg) dissolved in physiological solution of sodium chloride.

The activity of α-amylase in the serum was determined, from which there was calculated a ratio of the dilution of the serum required for neutralizing a given amount of α-amylase. The calculative value was indicated by the value of the antibody against α-amylase, viz, one unit of the antibody against α-amylase corresponds to the ratio of the dilution of the serum which is able to neutralize just 10 units of α-amylase activity. The results are shown in Table 2 where a known trehalolipid and a system without addition of the glycolipid are used for reference and control purposes respectively.

TABLE 2

Antibody value against α-amylase (unit) in the serum

|  | Guinea Pig | Antibody value (unit) | Average value |
|---|---|---|---|
| Trehalolipid | 1 | 1141 | 1250 ± 91 |
| (mycalic acid) | 2 | 1498 | (44.6) |
| (reference) | 3 | 1097 |  |
|  | 4 | 1266 |  |
| Sucrolipid | 1 | 313 | 176 ± 47 |
| (corynomycolic | 2 | 162 | (6.3) |
| acid) | 3 | 116 |  |
|  | 4 | 111 |  |
| Glucolipid | 1 | 133 | 99 ± 21 |
| (Mycolic acid) | 2 | 72 | (3.5) |
|  | 3 | 69 |  |
|  | 4 | 55 |  |
| Fructolipid | 1 | 347 | 264 ± 50 |
| (mycolic acid) | 2 | 314 | (9.5) |
|  | 3 | 235 |  |
|  | 4 | 162 |  |
| Fructolipid | 1 | 265 | 176 ± 61 |
| (corynomycolic | 2 | 175 | (6.3) |
| acid) | 3 | 87 |  |
|  | 4 | not measured |  |
| Without addition | 1 | 43 | 28 ± 8 |
| of glycolipid | 2 | 26 | (1.0) |
| (control) | 3 | 17 |  |

EXAMPLE 3

Glycolipids shown in Table 3 were used for the test. A glycolipid (100 μg), phytohemagglutinin (500 μg; commercially available from Difco Laboratories, U.S.A.) and Freund's incomplete adjuvant (0.05 ml) were mixed together and the mixture was administered to each test animal by subcutaneous injection into the right hind paw. Some groups of mice, each consisting of 10 mice (weight 20.5 g in average) were used as test animals and immunized in this manner. After 12 days from the injection, phytohemagglutinin (20 μg) was subcutaneously injected into the left hind paw. After 24 hours, the thickness of the left paw was measured and compared with the thickness before injection. The difference was used to determine the strength of the delayed-type hypersensitive reaction. In Table 3 showing the results, a known trehalolipid was used for reference purpose and also a system without addition of the glycolipid was used as control.

TABLE 3

|  | Delayed-type hypersensitive reaction (1/10 mm) |
| --- | --- |
| Trehalolipid (mycolic acid) | 8.2 |
| Sucrolipid (corynomycolic acid) | 3.5 |
| Glucolipid (mycolic acid) | 4.9 |
| Fructolipid (mycolic acid) | 7.8 |
| Fructolipid (corynomycolic acid) | 4.0 |
| Control (without addition of glycolipid) | 2.1 |

EXAMPLE 4

Test on the lysis of target cells

Glycolipids shown in Table 4 were used for the test. Tumor cells ($2 \times 10^4$/ml) of mastocytoma P 815 were mixed with an oil-in-water type mixture prepared in a similar manner to that described in Example 2 except that α-amylase was not used.

The mixture was administered to each of the test animals by intraperitoneal injection. Some groups of mice, each consisting of 4 mice (weight 30 g in average), were used for this purpose. After 14 days the spleen cells of the test animals were excised. The spleen cells (one ml containing $1 \times 10^7$ cells) were mixed with mastocytoma P815 (one ml containing $1 \times 10^5$ cells) labelled with radioactive chrome ($^{51}$chrome) and were incubated at 37° C. for 20 hours. The evolved amount of $^{51}$Cr was counted by a well-type scintillation counter. The degree of the lysis of the target cells was indicated by a ratio of the amount of the evolved radioactive chrome to the radio-activity in total. In Table 4 showing the results, a known trehalolipid and a mixture which does not contain the glycolipid are used for reference and control purposes respectively.

TABLE 4

|  | Ratio of the lysis of target cells (%) |
| --- | --- |
| Trehalolipid (mycolic acid)** | 68 |
| Sucrolipid (corynomycolic acid) | 30 |
| Glucolipid (mycolic acid) | 65 |
| Fructolipid (mycolic acid) | 55 |
| Fructolipid (corynomycolic acid) | 38 |
| Control (without addition of glycolipid) | 8 |

**Reference

EXAMPLE 5

The acute toxicities of the glycolipids according to the present invention were investigated in the following manner. Glycolipids shown in Table 5 were used in the test. As test animals, some groups of mice, each consisting of 5 male mice (weight 20.2 g in average), were used. A mixture of Tween 80 (a surfactant; 0.2 ml), physiological solution of sodium chloride (0.5 ml) and a glycolipid was administered to each of the test animals by intraperitoneal injection. The animals were observed for 14 days. The amount of the glycolipid in the mixture was changed from 150 mg/kg to 500 mg/kg through 250 mg/kg, and the results are shown in Table 5, from which it is apparent the acute toxicities of all of the glycolipids according to the present invention being more than 250 mg/kg.

TABLE 5

|  | 500 | 250 | 150 (mg/kg) |
| --- | --- | --- | --- |
| Sucrolipid (corynomycolic acid) | 1/5 | 0/5 | 0/5 |
| Glucolipid (mycolic acid) | 3/5 | 0/5 | 0/5 |
| Fructolipid (mycolic acid) | 0/5 | 0/5 | 0/5 |
| Fructolipid (corynomycolic acid) | 1/5 | 0/5 | 0/5 |

EXAMPLES 6-10

Immunotherapuetic effects of some glycolipid-containing compositions were investigated in the following manner. The glycolipid was prepared as described above. The glycolipid (100 γ) was suspended in a physiological solution of sodium chloride (0.1 ml) containing Tween 80 (0.2%; a commercial surfactant available from Atlas Chemical Industries Inc., U.S.A.). It was then suspended in another suspension composed of MEM medium (0.1 ml; a commercial product available from Nissui Seiyaku K.K., Japan, as Eagle MEM medium "Nissan") and $10^5$ of EL-4 leukemia cells. As test animals, groups of ten mice each of the same strain (weight 30±2 g; $C_{57}BL/6J$ strain), were used. A composition containing 100 γ of the glycolipid was intradermally administered to each test animal at the back.

After three weeks, the total number (A) of the surviving mice, and the number (B) denoting the number of surviving mice from which the symptoms of leukemia completely diminished were observed. The ratio of B/A shown in Table 6 illustrates the immunotherapeutic effects of the present compositions.

TABLE 6

| Example | Glycolipid (Origin) | Test mice | B/A |
| --- | --- | --- | --- |
| 6 | Glucolipid (M. avium) | 10 | 4/4 |
| 7 | Fructolipid (M. avium) | 10 | 5/5 |
| 8 | Fructolipid (M. rubra) | 10 | 0/0 |
| 9 | Fructolipid (A. paraffineus) | 10 | 2/2 |
| 10 | Sucrolipid (C. hydrocarboclastus) | 10 | 1/4 |
| Comparison | Trehalose (M. tuberculosis) | 10 | 2/2 |
| Comparison | Control (no glycolipid) | 10 | 0/2 |

EXAMPLES 11-12

A glycolipid prepared as described previously (100 γ) was suspended in a physiological solution of sodium chloride (0.1 ml) containing Tween 80 (0.2%). It was then mixed with another suspension composed of 0.1 ml of MEM medium and $10^5$ cells of fibrosarcoma (induced by using mice of $C_{57}BL/6J$ strain treated with 3-methyl-cholanthrene. As test animals, groups of 10 mice each of the same strain (weight 30±2 g; $C_{57}BL/6J$ strain) were used. A composition containing 100 γ of the indicated glycolipid was intradermally administered to each of the test mice at the back.

After three weeks, the total number (A) of the surviving mice, and the number (B) designating the surviving mice from which the symptoms of the sarcoma completely diminished were observed. The ratio of B/A shown in Table 7 illustrates the immunotherapeutic effects of the glycolipid-containing compositions according to the present invention.

TABLE 7

| Example | Glycolipid (Origin) | Test mice | B/A |
|---|---|---|---|
| 11 | Glucolipid (M. avium) | 10 | 0/9 |
| 12 | Fructolipid (M. avium) | 10 | 3/5 |
| Comparison | Trehalolipid (M. tuberculosis) | 10 | 0/3 |
| Comparison | Control (no glycolipid) | 10 | 0/2 |

Having set forth the present invention, that which is sought to be protected is set forth in the following claims.

We claim:

1. An adjuvant composition for enhancing immunization against a transplanted tumor which comprises a glycolipid as active ingredient in concentration of from 10 $\gamma$ to 10 mg/ml of composition, the saccharide moiety of said glycolipid being selected from fructose, sucrose and glucose, said composition further containing a pharmaceutically acceptable carrier.

2. A composition according to claim 1 in which the glycolipid is selected from the group consisting of a fructolipid of the formula [I], a sucrolipid of the formula [II] and a glucolipid of the formula [III]:

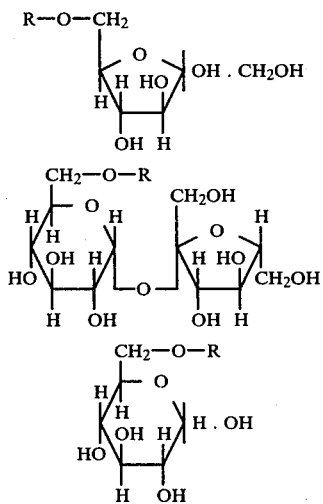

in which R is a residual group of an acid selected from the group consisting of mycolic acid, nocardomycolic acid and corynomycolic acid.

3. A composition according to claim 1, in which the glycolipid is produced by a microorganism.

4. A composition according to claim 2 wherein the acid is a fatty acid represented by the formula:

$$R_2-CH-CH-COOH$$
$$\;\;\;\;\;\;|\;\;\;\;\;|$$
$$\;\;\;\;\;OH\;\;R_1$$

in which $R_1$ and $R_2$ are alkyl groups.

5. A composition according to claim 1 having a glycolipid concentration of 100 $\gamma$ to 2 mg per ml.

6. A method for imparting immunotherapy against a transplanted tumor in an animal subject, which comprises administering into the body of a tumor-carrying animal a composition containing as an active ingredient a glycolipid, having a saccharide moiety selected from the group consisting of fructose, sucrose and glucose, said composition additionally containing a pharmaceutically acceptable carrier.

7. The method of claim 6, in which the glycolipid is selected from the group consisting of a fructolipid of the formula [I], a sucrolipid of the formula [II] and a glucolipid of the formula [III]:

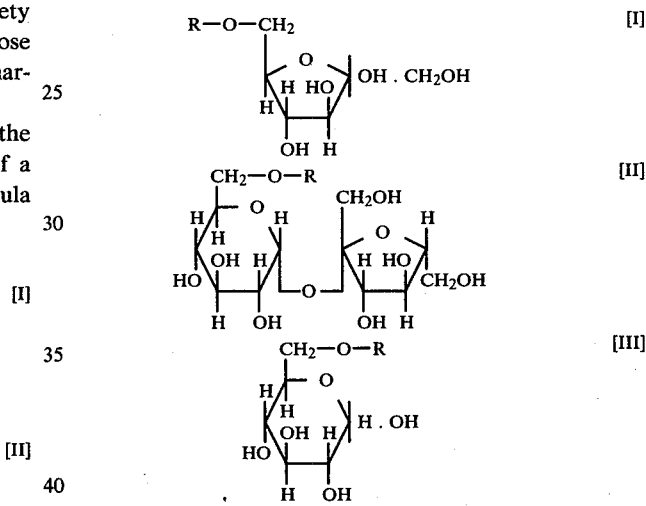

in which R is a residual group of an acid selected from the group consisting of mycolic acid, nocardomycolic acid and corynomycolic acid.

8. The method of claim 6 in which the glycolipid is administered at a rate of from 10 $\gamma$ to 10 mg in one week, based upon an average mammal approximately 60 kg.

9. The method of claim 6 wherein the composition is topically administered into a tumor in the body of the animal.

10. The method of claim 9 wherein the composition is administered in association with another agent for immunotherapy against tumor which originates from the cell wall of a microorganism.

11. The method of claim 10 wherein the cell walls are selected from the group consisting of *Propionibacterium acnes* cell walls, *Nocardia rubra* cell walls and BCG cell walls.

* * * * *